US012564493B2

(12) United States Patent
Keränen et al.

(10) Patent No.: US 12,564,493 B2
(45) Date of Patent: Mar. 3, 2026

(54) ANNULOPLASTY SYSTEM

(71) Applicant: Medtentia International Ltd Oy,
Espoo (FI)

(72) Inventors: Olli Keränen, Bjärred (SE); **Jani
Virtanen**, Söderkulla (FI)

( * ) Notice: Subject to any disclaimer, the term of this
patent is extended or adjusted under 35
U.S.C. 154(b) by 877 days.

(21) Appl. No.: 17/780,046

(22) PCT Filed: Nov. 30, 2020

(86) PCT No.: PCT/EP2020/083906
§ 371 (c)(1),
(2) Date: May 26, 2022

(87) PCT Pub. No.: WO2021/105500
PCT Pub. Date: Jun. 3, 2021

(65) Prior Publication Data
US 2023/0000625 A1     Jan. 5, 2023

(30) Foreign Application Priority Data
Nov. 29, 2019     (EP) ..................................... 19212603

(51) Int. Cl.
*A61F 2/24*          (2006.01)

(52) U.S. Cl.
CPC ............ *A61F 2/2445* (2013.01); *A61F 2/246*
(2013.01); *A61F 2/2466* (2013.01); *A61F*
*2230/0091* (2013.01)

(58) Field of Classification Search
CPC ...... A61F 2/2442; A61F 2/2445; A61F 2/246;
A61F 2/2463; A61F 2/2466
See application file for complete search history.

(56) References Cited

U.S. PATENT DOCUMENTS

| | | |
|---|---|---|
| 2011/0301699 A1 | 12/2011 | Saadat |
| 2012/0296419 A1 | 11/2012 | Richardson et al. |
| 2018/0177594 A1 | 6/2018 | Patel et al. |

*Primary Examiner* — William H Matthews
(74) *Attorney, Agent, or Firm* — Patent Grove AB; Tomas
Friend

(57) ABSTRACT

A system for annuloplasty is disclosed comprising an annu-
loplasty device comprising first and second support rings
having a coiled configuration in which the first and second
support rings are arranged as a coil around a central axis,
wherein the first and second support rings are configured to
be arranged on opposite sides of native heart valve leaflets
of a heart valve, a line attached to the first and/or second
support ring, and a heating element configured to be heated
upon receiving a supply of energy, wherein the heating
element is positionable to heat and sever the line upon the
heating element receiving said energy.

17 Claims, 8 Drawing Sheets

ANNULOPLASTY SYSTEM

TECHNICAL FIELD

This invention pertains in general to the field of cardiac valve replacement and repair. More particularly the invention relates to an annuloplasty system for delivery of an annuloplasty device to a cardiac valve.

BACKGROUND

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty device, such as an annuloplasty ring, to reduce the diameter of the annulus, or modify the geometry of the annulus in any other way, or aid as a generally supporting structure during the valve replacement or repair procedure. Such annuloplasty devices are implanted into position by various delivery devices.

A problem with prior art devices are less-than-optimal engagement and deployment mechanisms between the annuloplasty device and the delivery device which does not provide sufficient reliability during the positioning phase and during deployment to get the annuloplasty device in the final secured position, which may lead to a more complicated and time consuming procedure. Previous devices thus require exact, i.e. time consuming, navigation and manipulation to minimize the risk of sub-optimal fixation of the annuloplasty device. During heart surgery, a premium is placed on reducing the amount of time used to replace and repair valves as the heart is frequently arrested and without perfusion. The above problems may have dire consequences for the patient and the health care system. Patient risk is increased. A problem with prior art devices seeking to improve upon the mentioned disadvantages is increased complexity of the deployment mechanisms between the annuloplasty device and the delivery device. This leads to less cost-effectiveness, and/or lack of a compact cross-sectional profile which typically has a negative impact on the steerability of the annuloplasty device and an overall more cumbersome navigation of the annuloplasty device to its final position.

Hence, an improved annuloplasty system for delivery and implantation of an annuloplasty device at a cardiac valve would be advantageous and in particular allowing for avoiding more of the above mentioned problems and compromises, and in particular allowing for a more secure implantation procedure and reducing the time of lengthy surgery procedures, and increased patient safety.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect a system for annuloplasty is provided comprising an annuloplasty device comprising first and second support rings having a coiled configuration in which the first and second support rings are arranged as a coil around a central axis, wherein the first and second support rings are configured to be arranged on opposite sides of native heart valve leaflets of a heart valve, a line attached to the first and/or second support ring, and a heating element configured to be heated upon receiving a supply of energy, wherein the heating element is positionable to heat and sever the line upon the heating element receiving said energy.

According to a second aspect a method for delivering an annuloplasty device is provided comprising positioning first and second support rings of the annuloplasty device on opposite sides of native heart valve leaflets of a heart valve, positioning a heating element adjacent a line attached to the first and/or second support ring, supplying energy to the heating element to heat and sever the line, and withdrawing the heating element from the heart valve.

Further examples of the invention are defined in the dependent claims, wherein features for the second and subsequent aspects of the disclosure are as for the first aspect mutatis mutandis.

Some examples of the disclosure provide for implanting an annuloplasty device more securely.

Some examples of the disclosure provide for an annuloplasty device which is easier to reposition during an implantation procedure.

Some examples of the disclosure provide for a less time consuming deployment and positioning of an annuloplasty device at a cardiac valve.

Some examples of the disclosure provide for a less cumbersome detachment of an annuloplasty device to a delivery device.

Some examples of the disclosure provide for increased accuracy in positioning an annuloplasty device at the annulus of a cardiac valve and thereby reducing the risk of complications.

Some examples of the disclosure provide for a reduced risk of damaging the cardiac valve during a repair or replacement procedure.

Some examples of the disclosure provide for increased steerability or maneuverability of the annuloplasty device.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the invention are capable of will be apparent and elucidated from the following description of embodiments of the present invention, reference being made to the accompanying drawings, in which.

DETAILED DESCRIPTION

Figure 1:
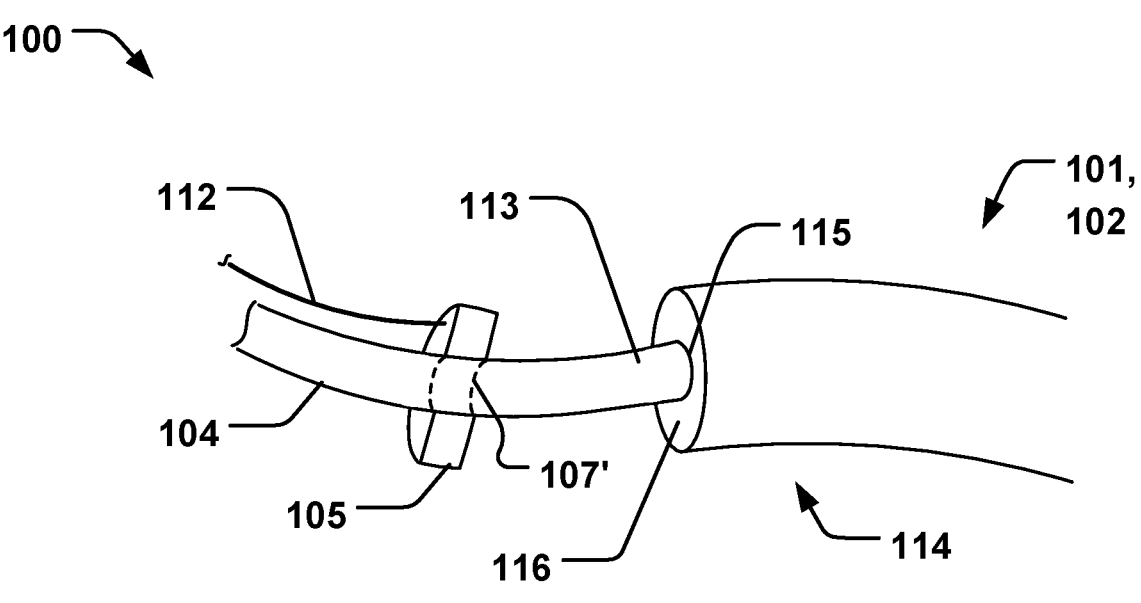
FIG. 1 is a schematic illustration of an annuloplasty system according to one example.

Specific examples of the invention will now be described with reference to the accompanying drawings. This invention may, however, be embodied in many different forms and should not be construed as limited to the examples set forth herein; rather, these examples are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on examples applicable to cardiac valve devices such as annuloplasty rings. However, it will be appreciated that the invention is not limited to this application but may be applied to many other annuloplasty implants and cardiac valve implants including for example replacement valves, and other medical implantable devices.

Figure 12:
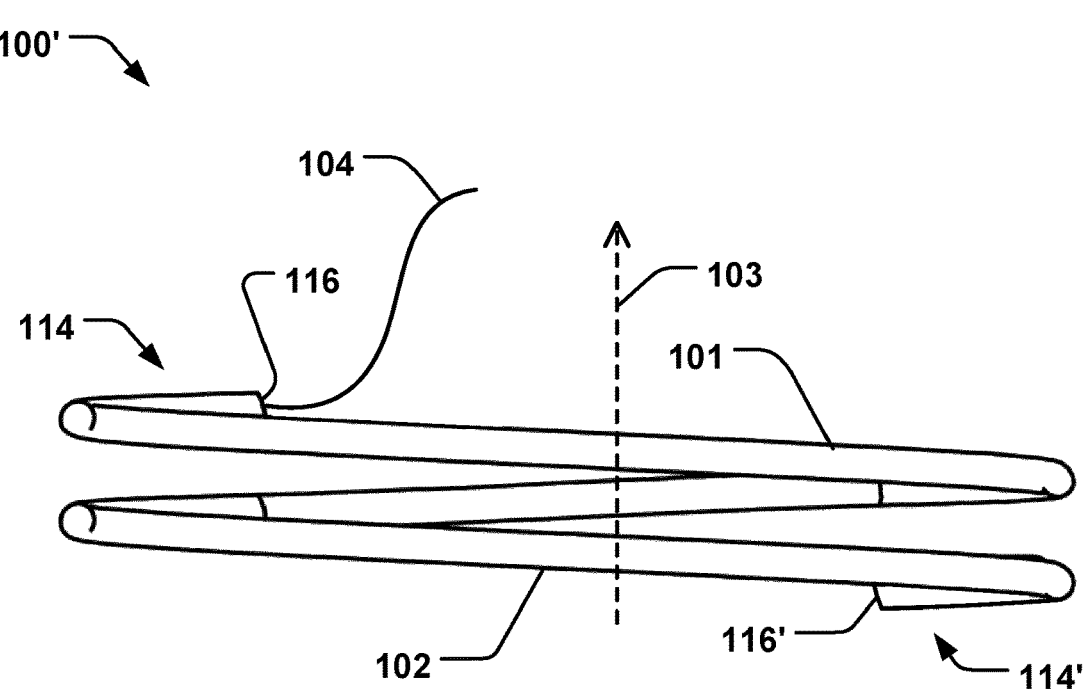
FIG. 12 is a schematic illustration of an annuloplasty device, in a side view, according to one example.
Figure 13:
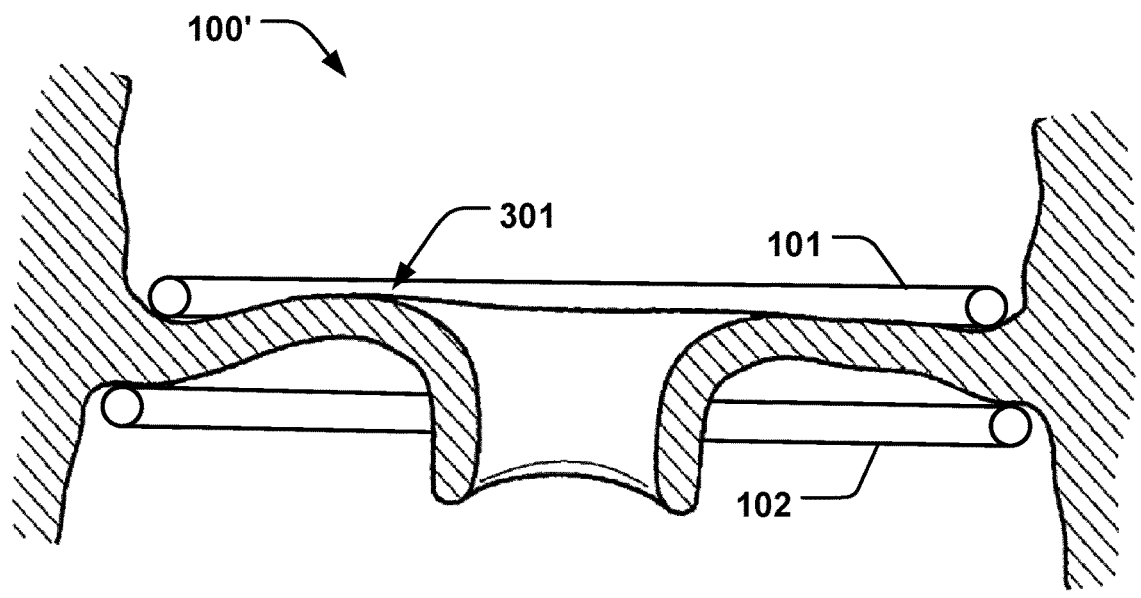
FIG. 13 is a schematic illustration of an annuloplasty device, in a side view, where the annuloplasty device is positioned above and below valve leaflets, according to one example.

FIG. 12 schematically illustrates an example of an annuloplasty device 100' comprising a first support ring 101 and second support ring 102 which are adapted to be arranged as a coil, i.e. in a helix-shape, in a coiled configuration around a central axis 103. The annuloplasty device 100' is arranged in the coiled configuration at least when in a relaxed state of the material from which the annuloplasty device 100' is formed, i.e. free from outside forces acting upon the annuloplasty device 100'. The first and second support rings 101, 102, are configured to be arranged on opposite sides of native heart valve leaflets 301 of a heart valve, as illustrated in the side view of FIG. 13. As shown in FIG. 13, the first support ring 101 may be arranged on an atrial side of the heart valve, around the annulus of the valve, and the second support ring 102 may be arranged on a ventricular side. The first and second support rings 101, 102, are connected to form a coil- or helix shaped ring. The coil extends through the valve opening at a commissure thereof. The first and second support rings 101, 102, may thus assume the coiled configuration also when in an implanted state. The annuloplasty device 100' may comprise a shape-memory material, so that the annuloplasty device 100' re-assumes the coiled configuration after having been delivered from a delivery device (not shown), such as a delivery catheter, to the target site, after having been temporarily restrained in an elongated configuration inside such catheter. The annuloplasty device 100', i.e. annuloplasty implant 100', may comprise a shape memory material, such as NiTiNol, or another suitable biocompatible alloy that can be heat-set in defined shapes, i.e. in a defined relaxed shape in absence of outside acting forces, such as in a coiled configuration, in a heat treatment procedure.

Figure 2:
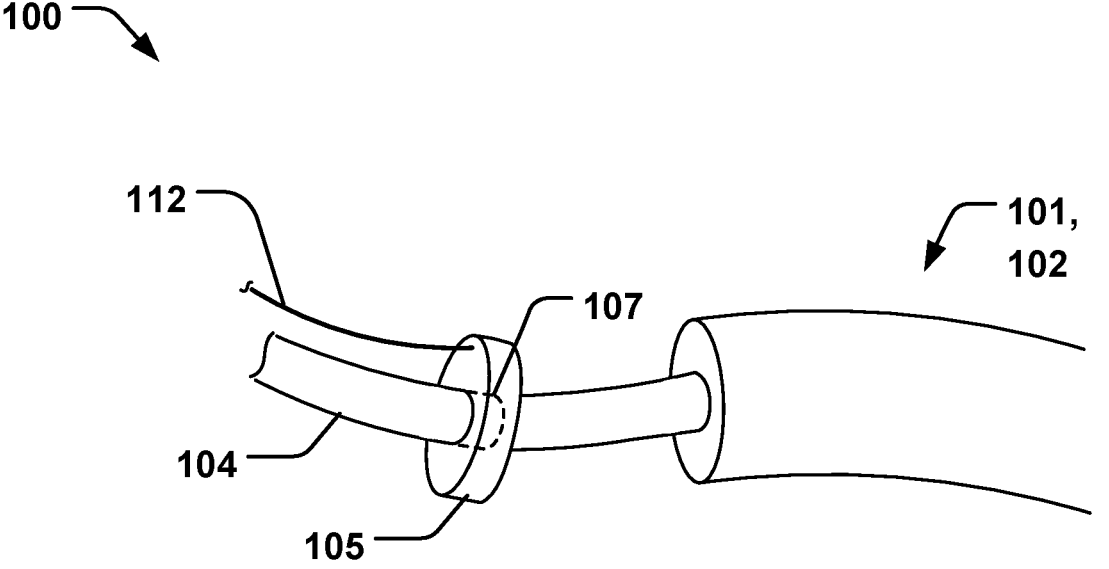
FIG. 2 is a schematic illustration of an annuloplasty system according to one example.
Figure 3:
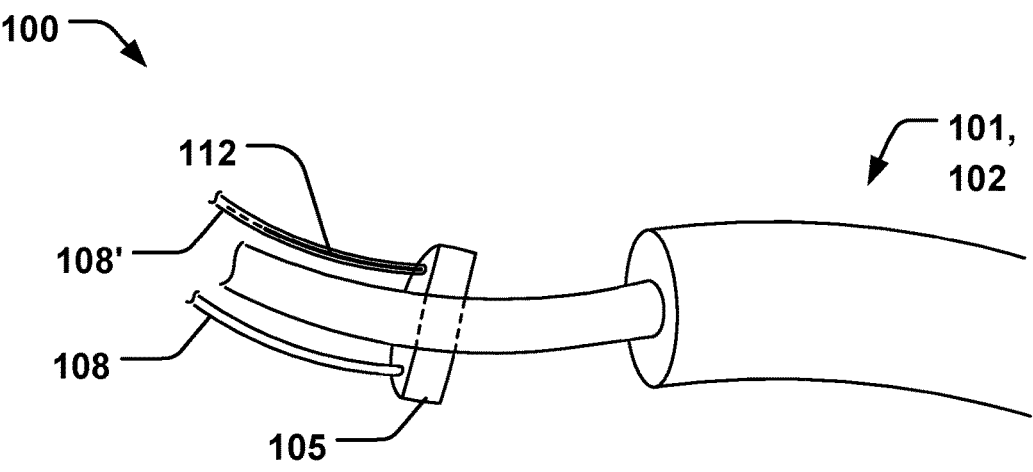
FIG. 3 is a schematic illustration of an annuloplasty system according to one example.
Figure 4:
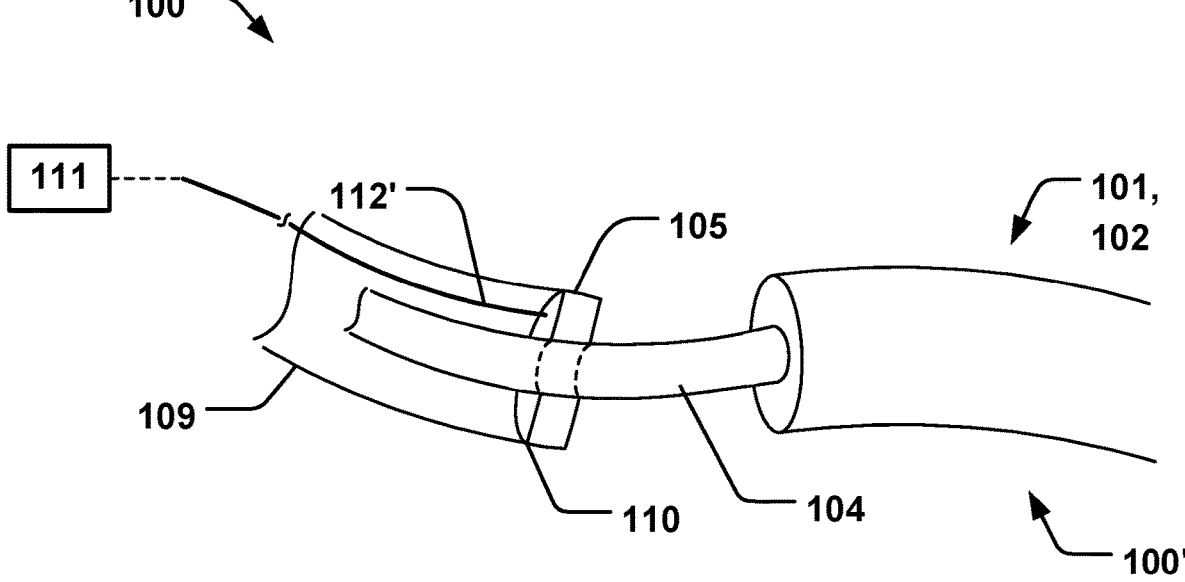
FIG. 4 is a schematic illustration of an annuloplasty system according to one example.
Figure 5:
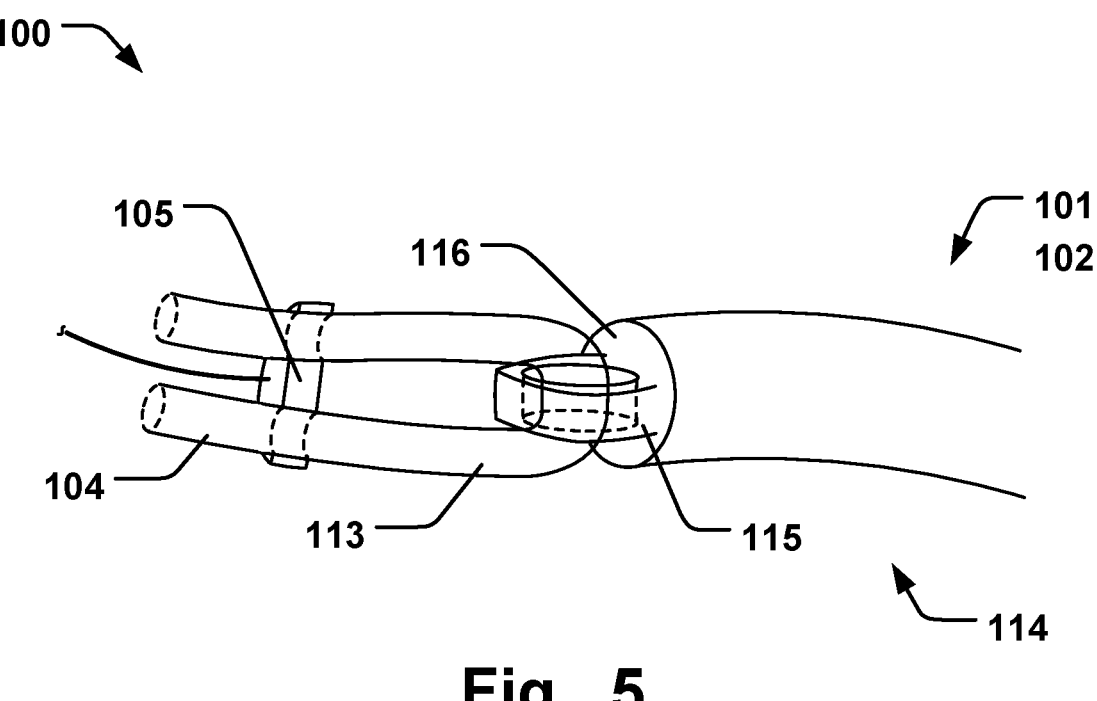
FIG. 5 is a schematic illustration of an annuloplasty system according to one example.

FIGS. 1-11 show examples of a system 100 for annuloplasty, i.e. for delivery of an annuloplasty device 100', such as an annuloplasty device 100' described above. The system 100 thus comprises an annuloplasty device 100', and the annuloplasty device 100' comprises first 101 and second 102 support rings having a coiled configuration in which the first and second support rings are arranged as a coil around a central axis 103. The first and second support rings are configured to be arranged on opposite sides of native heart valve leaflets 301 of a heart valve. FIGS. 1-11 show only part of the annuloplasty device 100', i.e. by showing a part of the first or second support ring 101, 102, for a clearer presentation in the figures. The system 100 comprises a line 104 attached to the first and/or second support ring 101, 102. The line may 104 may be a suture, wire, or any other essentially flexible and elongated element sized to be arranged in, and/or connect to, a delivery device 109, as shown in the example of FIG. 4. The system 100 further comprises a heating element 105 configured to be heated upon receiving a supply of energy, such as a current supply or a magnetic field for inducing a current in the heating element 105, as discussed further below. The heating element 105 is positionable to heat and sever the line 104 upon the heating element 105 receiving said energy. The heating element 105 may be moved into position, where the line 104 is to be cut, by a delivery device 109 as discussed in relation to e.g. FIG. 4 and or by any other control element, such as a control wire 108, 108', as discussed in relation to e.g. FIG. 3. Thus, the heating element 105 can be position in contact with the line 104, or in sufficiently close proximity with the line 104 to heat and melt the material from which the line 104 is formed, thereby severing the line 104. The first and second support ring 101, 102, is thereby released from the line 104 and may be fixed to the cardiac valve. This provides for an effective and robust release mechanism for the annuloplasty device 100'. The implantation procedure may thus be completed in a less amount of time, while maintaining an advantageous safety mechanism by having a connection to the annuloplasty device 100' with a line 104 as long as possible. E.g. repositioning is facilitated by manipulation of the line 104. The position of the first and second support rings 101, 102, at the cardiac valve may be changed by e.g. pulling of the line 104, to optimize the respective positions on the ventricular and atrial side. The line 104 also provides for fully withdrawing the first and second support rings 101, 102, from the implantation site in case of complications. A more secure implantation of the annuloplasty device 100' is thus provided. Having a heating element 105 to heat and sever the line 104 for releasing the annuloplasty device 100' provides also for a less complex delivery mechanism and a minimized cross-section of the annuloplasty system 100 in a radial direction 119 (FIG. 11), i.e. in a direction perpendicular to the longitudinal direction 117 in which the first and second support rings 101, 102, generally extend. The compact cross-section facilitates integration with existing delivery devices, and the procedure may be completed with less components and with fewer steps.

The heating element 105 may comprise a resistor, also denoted with reference numeral 105 in e.g. FIG. 1, being configured to receive the energy as electrical energy for heating of the resistor. The resistor 105 may receive an electrical current via a conductor 112, as schematically shown in e.g. FIG. 1. This provides for an efficient heating of the line 104, for melting and cutting the line 104 in a short amount of time.

In another example, the heating element 105 may comprise an electrically conductive material, and the heating element 105 may receive energy from a fluctuating magnetic field. The electrically conductive material may thus be arranged so that the magnetic field induces a current in the heating element 105 to heat the heating element 105. Such inductive heating of the heating element 105 may be advantageous in some applications. This may in some examples provide for a facilitated positioning of the heating element 105 at the desired position relative the line 104. The aforementioned conductor 112 may be dispensed with in such case. Thus, eventhough the examples in FIGS. 1-8, 10-11, indicate having a conductor 112 coupled to the heating element 105, it is conceivable that the heating element 105 may be heated by inductive heating in these examples.

Figure 9A:
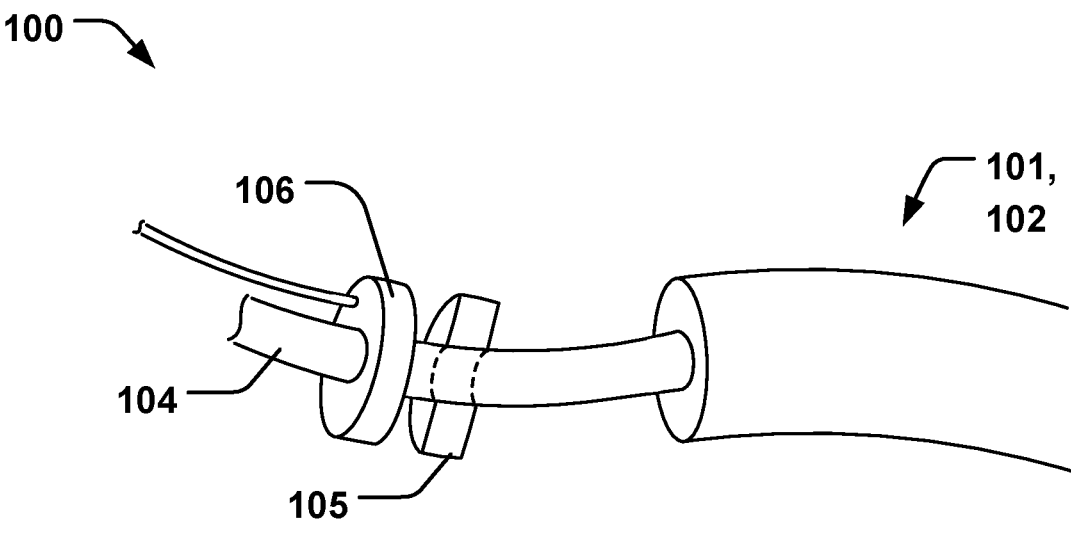
FIGS. 9a-b are schematic illustrations of an annuloplasty system according to examples of the disclosure.
Figure 9B:
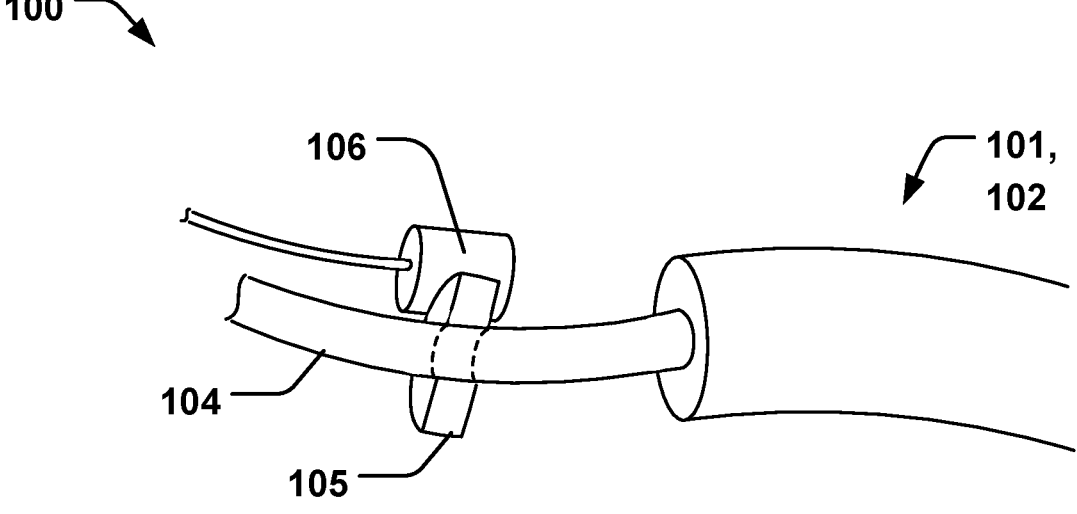

The annuloplasty system 100 may comprise an inductor 106 arranged to induce said current in the heating element 105. The inductor 106 may thus be supplied by an alternating current which produces a varying magnetic field of a magnetizable core material of the inductor 106. The inductor 106 is positionable adjacent the heating element 105 so that currents are generated by the varying magnetic field in the conductive material of the heating element 105. The currents flowing through the resistance of the conductive material heats the heating element 105. FIG. 9*a* is a schematic illustration showing an inductor 106 positioned adjacent the heating element 105. The inductor 106 may have varying shapes such as round or oval as in the example of FIG. 9*a*. The line 104 may pass through the inductor 106, as further exemplified in FIG. 9*a*. FIG. 9*b* show another example where the inductor 106 is elongated and cylindrically shaped, and positioned at the side of the line 104 and adjacent the heating element 105. The inductor 106 may be movable along the line 104 as a separate element or be integrated with a delivery device 109.

Figure 6:
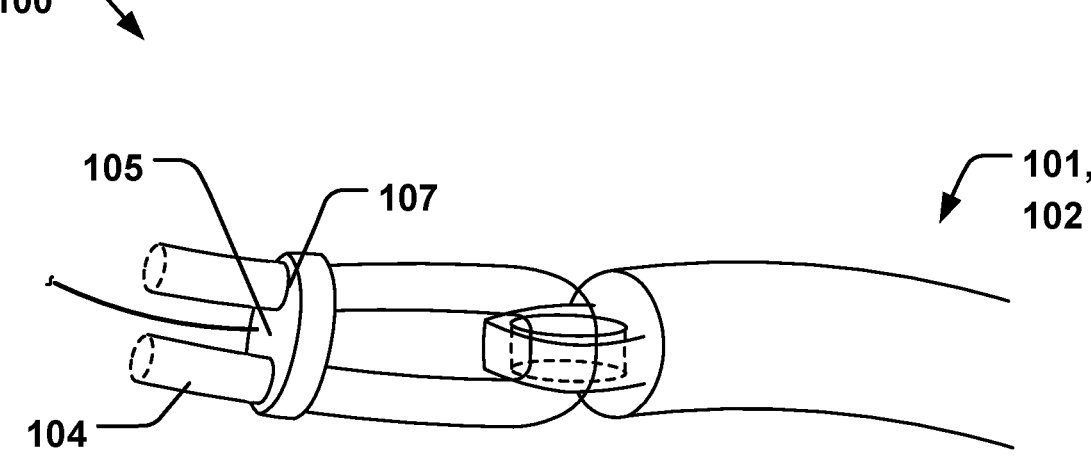
FIG. 6 is a schematic illustration of an annuloplasty system according to one example.
Figure 7:
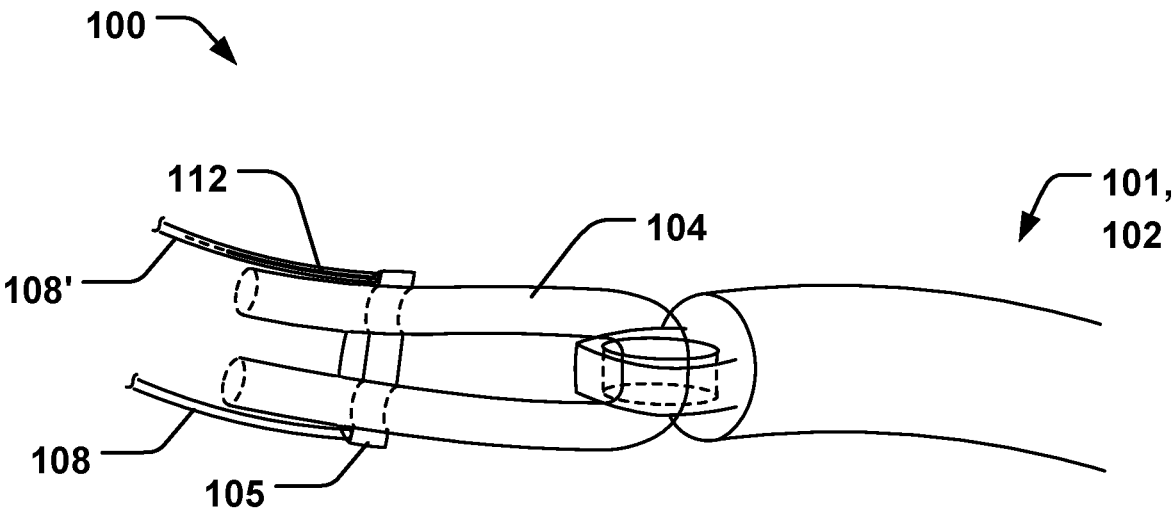
FIG. 7 is a schematic illustration of an annuloplasty system according to one example.
Figure 8:
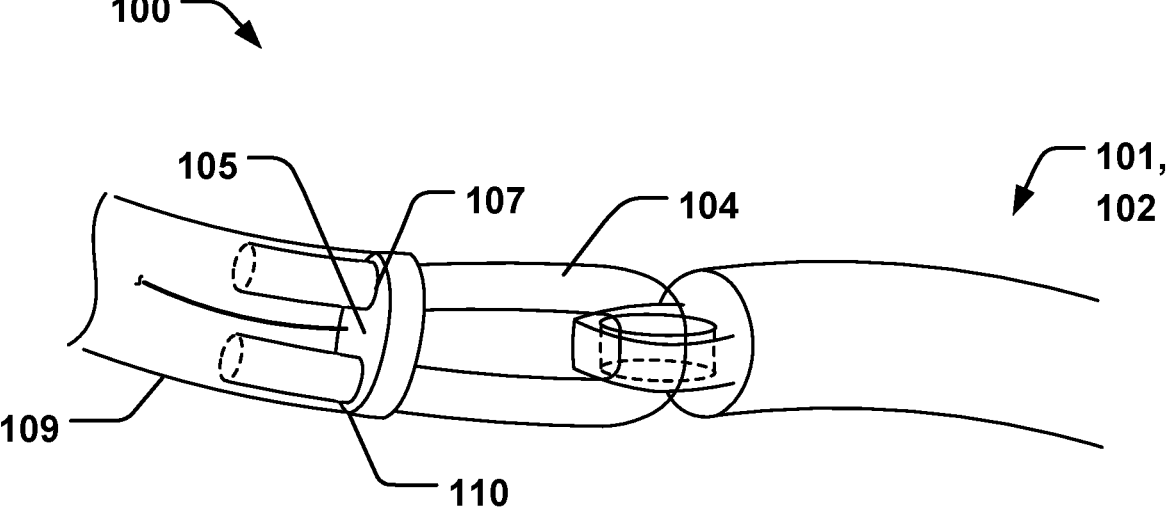
FIG. 8 is a schematic illustration of an annuloplasty system according to one example.

The heating element 105 may comprise at least one aperture 107 through which the line 104 may be arranged, as schematically illustrated in the examples of FIGS. 2, 6 and 8. The heating element 105 may thus be guided by the line 104 itself when advanced into the desired position where the line is to be cut. This may be advantageous in some applications and may provide for facilitated positioning of the heating element 105. FIG. 2 show an example where a single aperture 107 is provided in the heating element 105, while FIGS. 6 and 8 have two apertures 107 through which a looped line 104 may extend. In other examples, the heating element 105 may have a guiding groove 107' which is shaped to conform at least partly to the cross-section of the line 104, such as schematically illustrated in FIGS. 1, 4, 5, 7, 9*a-b*, and 11. This provides for guiding of the heating element 105 to the desired position, while also maintaining the possibility of engaging and disengaging with the line 104 sideways by not being constrained by an aperture thereof, which may be advantageous in some applications. The heating element 105 may in other examples be positionable adjacent the line 104 without any aperture or guiding groove thereof, such as schematically shown in FIG. 3 where the heating element is positioned with an essentially flat surface against the line 104. This may be advantageous in some examples, e.g. when it is desired to minimize any friction between the line 104 and the heating element 105 and facilitate advancement of the latter to the desired position. The heating element 105 may have different shapes, such as round or oval, and/or elongated, e.g. as shown in the examples of FIGS. 1-11. It should be understood that also different shapes are conceivable depending on the particular application while generally providing for the above mentioned advantageous benefits of the annuloplasty system 100.

The heating element 105 may thus be movable along the line 104. The heating element 105 may be connected to a control wire 108, 108', to move the heating element 105 along the line 104. FIG. 3 show a schematic example of having control wires 108, 108', connected to the heating element 105 although it should be understood that a single control wire 108 may be sufficient in some examples. The control wire 108, 108', may extend through a delivery device 109. One or more of the control wires may also comprise a conductor 112 for supplying a current to the heating element 105, as schematically indicated in FIG. 3.

The annuloplasty system 100 may comprise a delivery device 109, as schematically shown in FIG. 4. The annuloplasty device 100', i.e. the first and second support rings 101, 102, may be delivered from the delivery device 109, and the line 104 may also extend through the delivery device 109. The delivery device 109 may alternatively be utilized as a pusher to push the annuloplasty device 100' distally to eject the first and second support rings 101, 102, from a surrounding delivery catheter (not shown). The heating element 105 may be attached to a distal end 110 of the delivery device 109. Having the heating element 105 attached to the delivery device 109 may be advantageous in some applications where it is beneficial to omit a separate control wire 108, 108'. It should be understood that any of the heating elements 105 shown in the examples of FIGS. 1-11 may be attached to a distal end 110 of a delivery device 109. Furthermore, having the heating element 105 attached to a distal end 110 provides for a facilitated positioning of the heating element 105 as close as possible to the first or second support ring 101, 102, for cutting the line 104. I.e. the length of the remaining piece of the line 104 attached to the first or second support ring 101, 102, may be minimized.

The heating element 105 may be connected to a power supply 111 by a conductor 112' extending along the delivery device 109, as schematically illustrated in the example of FIG. 4. Alternatively, if having the heating element 105 heated by inductive heating, the inductor 106 (FIGS. 9*a-b*) may be connected to the power supply 111.

Figure 10:
FIG. 10 is a schematic illustration of an annuloplasty system according to one example.
Figure 10:
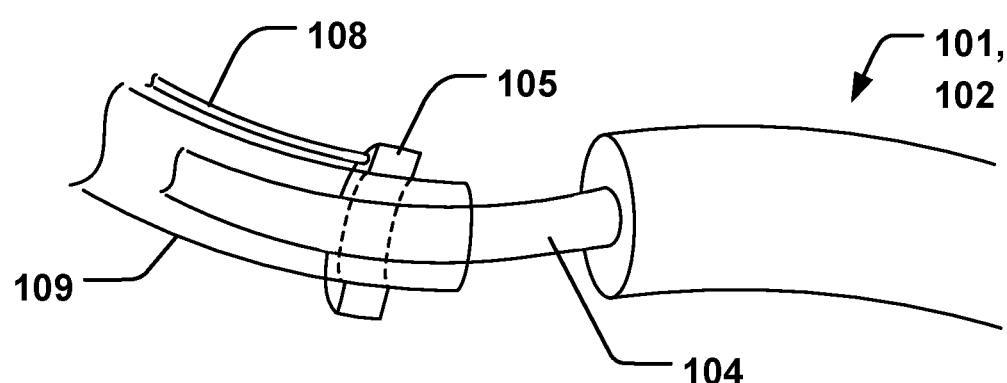

In another example, the heating element 105 may be movable over the delivery device 109, as schematically illustrated in FIG. 10. The delivery device 109 may thus guide the heating element 105 into the desired position to cut the line 104, while maintaining an open interior lumen of the delivery device 109, e.g. for deployment of the annuloplasty device 100' and associated line 104. In the example shown in FIG. 10, the heating element 105 is illustrated in a position over the delivery device 109 and it should be understood that the heating element 105 may be advanced closer to the exposed section of the line 104 for heating and severing the latter. A control wire 108 may be connected to the heating element 105 for moving the latter along the outside of the delivery device 109.

A distal end 113 of the line 104 may be attached to a free end 114 of the first or second support ring 101, 102, as schematically shown in e.g. FIG. 1. The coil-shaped annuloplasty device 100' has two free ends 114, 114', as schematically shown in FIG. 12. FIG. 12 show a schematic example where the line 104 is attached to a free end 114, of the first support ring 101. In the examples illustrated in FIGS. 1-11 it should be understood that the line 104 may be attached to the free end 114 of the first support ring 101, or the free end 114' of the second support ring 102. Having the line 104 attached to the free end 114, 114' provides for a facilitated positioning, repositioning, or withdrawal of the annuloplasty device 100' if required. The line 104 being attached to the free end 114, 114', should be construed as a line 104 being securely fixed to the annuloplasty device 100' such that, in use, pulling the line 104 towards a delivery device, such as a catheter, allows the first and second support rings 101, 102, to be withdraw towards such catheter, and thus allowing for retrieval of the annuloplasty device 100' after being previously deployed from such delivery catheter.

Figure 11:
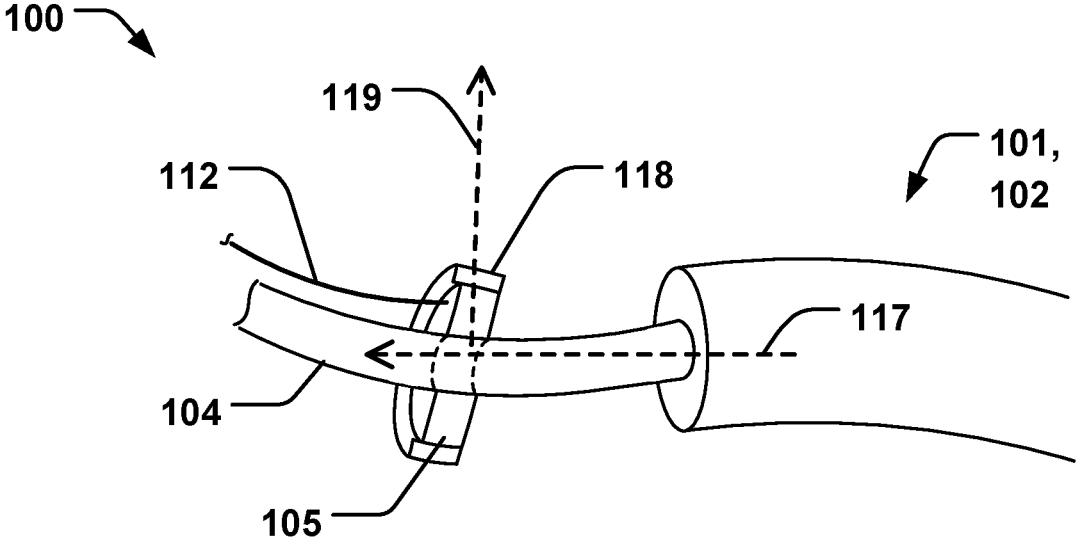
FIG. 11 is a schematic illustration of an annuloplasty system according to one example.

The distal end 113 of the line 104 may be attached at a proximal connection 115 at a proximal tip 116 of the free end 114, 114', as schematically illustrated in e.g. FIG. 1. The first and second support rings 101, 102, and the free ends 114, 114', thereof extends generally along a longitudinal direction 117 (FIG. 11). The proximal tip 116 of the free end 114, 114', should be construed as the part of the free end 114, 114', such as a surface of the free end, which terminates the free end 1114, 114', along the longitudinal direction 117. The proximal connection 115 fixedly attaches the line 104 to the proximal tip 116. Having a line 104 attached to the proximal tip 116 provides for a secure retrieval of the first and second support rings 101, 102, while minimizing the cross-section of the annuloplasty device 100' in a direction perpendicular to the longitudinal direction 117, i.e. in a radial direction 119 (FIG. 11). The minimized cross-section provided by proximal connection at the proximal tip 116 allows for an improved maneuverability and facilitated positioning of the first and second support rings 101, 102, at the valve. The compact cross-section facilitates integration with existing delivery devices, and the procedure may be completed with less components and with fewer steps.

The heating element 105 may be movable to contact the proximal tip 116. This provides for minimizing the remaining length of the line 104, attached to the first or second support ring 101, 102, after being cut by the heating element 105.

The first and second support rings 101, 102, and the line 104 hence extend generally along a longitudinal direction 117. The system 100 may comprise a heat shield 118 arranged radially outside the heating element 105, along a radial direction 119 which is perpendicular to the longitudinal direction 117, as schematically illustrated in FIG. 11. The heat shield 118 thus covers the heating element 105 along the longitudinal direction 117. This provides for minimizing the risk of damaging surrounding tissue from the heat of the heating element 105.

The heating element 105 may be elongated along the radial direction 119, i.e. perpendicular to the longitudinal direction 117, as schematically shown in e.g. FIG. 11 or FIG. 1. This provides for limiting the footprint of the heating element 105 along the longitudinal direction 117 and concentration of the heat to a reduced length of the line 104 along the longitudinal direction 117 so that a distinct cut is provided, with a minimum of melted material of the line 104.

Figures 14A, 14B:
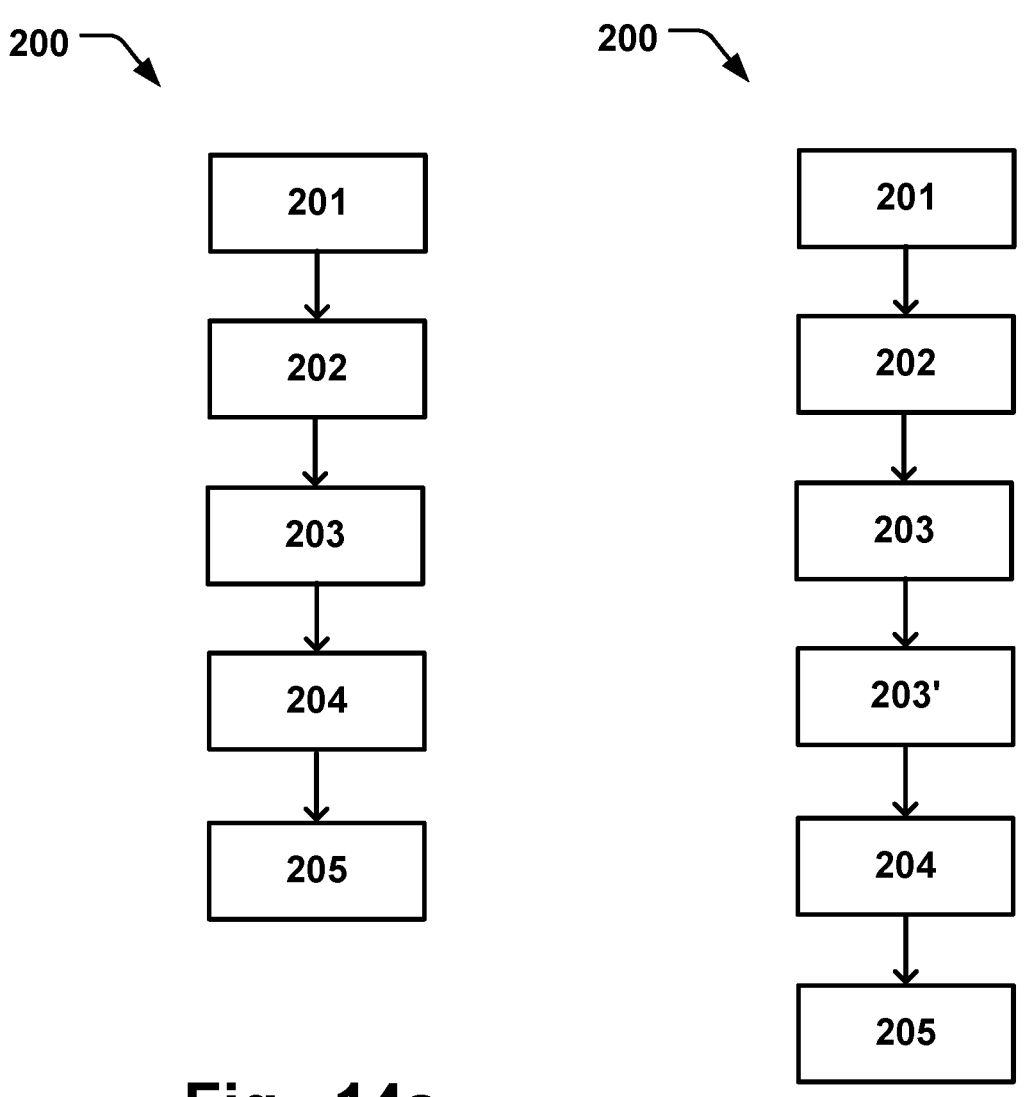
FIGS. 14a-b are flow charts of a method for delivering an annuloplasty device, according to examples of the disclosure.

FIG. 14a shows a flowchart of a method 200 for delivering an annuloplasty device 100'. The method 200 comprises positioning 201 first and second support rings 101, 102 of the annuloplasty device 100' on opposite sides of native heart valve leaflets 301 of a heart valve; positioning 202 a heating element 105 adjacent a line 104 attached to the first and/or second support ring 101, 102; supplying 203 energy to the heating element 105 to heat and sever 204 the line 104; withdrawing 205 the heating element 105 from the heart valve. The method 200 thus provides for the advantageous benefits as described above in relation to FIGS. 1-11 for the annuloplasty system 100.

FIG. 14b show another flowchart of a method 200 for delivering an annuloplasty device 100'. As described above, the heating element 105 may comprise a resistor. The method 200 may thus comprise supplying 203' electrical energy to the resistor for heating the resistor to sever the line.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A system for annuloplasty, said system comprising:
an annuloplasty device comprising a first support ring and a second support ring, said first and second support rings having a coiled configuration in which the first and second support rings are arranged as a coil around a central axis, wherein the first and second support rings are configured to be arranged on opposite sides of native heart valve leaflets of a heart valve;
a line attached to the first support ring and/or the second support ring; and
a heating element configured to be heated upon receiving a supply of energy, wherein the heating element is positionable to heat and sever the line upon the heating element receiving said energy.

2. The system according to claim 1, wherein the heating element comprises a resistor configured to receive the energy as electrical energy for heating of the resistor.

3. The system according to claim 1, wherein:
the heating element comprises an electrically conductive material;
the energy is a fluctuating magnetic field; and
the electrically conductive material is arranged so that the magnetic field induces a current in the heating element to heat the heating element.

4. The system according to claim 3, wherein the system comprises an inductor arranged to induce said current in the heating element.

5. The system according of claim 1, wherein the heating element comprises at least one aperture through which the line is arranged.

6. The system according to claim 5, wherein the heating element is movable along the line.

7. The system according to claim 1, wherein the heating element is connected to a control wire to move the heating element along the line.

8. The system according to claim 1, further comprising a delivery device and wherein the heating element is attached to a distal end of the delivery device.

9. The system according to claim 8, wherein the heating element is connected to a power supply by a conductor extending along the delivery device.

10. The system according to claim 1, wherein the heating element is movable over the delivery device.

11. The system according to claim 1 wherein a distal end of the line is attached to a free end of the first or second support ring.

12. The system according to claim 11, wherein the distal end of the line is attached at a proximal connection at a proximal tip of the free end.

13. The system according to claim 12, wherein the heating element is movable to contact the proximal tip.

14. The system according to claim 1, wherein the first and second support rings and the line extend generally along a longitudinal direction and the system comprises a heat shield arranged radially, outside the heating element, along a radial direction perpendicular to the longitudinal direction, and wherein the heat shield covers the heating element along the longitudinal direction.

15. The system according to claim 1, wherein the first and second support rings and the line extend generally along a longitudinal direction and the system comprises a heat shield, wherein the heat shield is elongated along a radial direction perpendicular to the longitudinal direction.

16. A method for delivering an annuloplasty device, said method comprising:

positioning first and second support rings of the annuloplasty device on opposite sides of native heart valve leaflets of a heart valve;

positioning a heating element adjacent a line attached to the first and/or second support ring;

supplying energy to the heating element to heat and sever the line; and withdrawing the heating element from the heart valve.

17. The method according to claim 16, wherein the heating element comprises a resistor and the method comprises supplying electrical energy to the resistor for heating the resistor to sever the line.

\* \* \* \* \*